(12) United States Patent
Budolfsen et al.

(10) Patent No.: US 7,396,670 B2
(45) Date of Patent: *Jul. 8, 2008

(54) ASPARAGINASES AND METHOD OF PREPARING A HEAT-TREATED PRODUCT

(75) Inventors: Gitte Budolfsen, Frederiksberg (DK); Morten Tovborg Jensen, Vaerlose (DK); Hans Peter Heldt-Hansen, Virum (DK); Mary Ann Stringer, Soborg (DK)

(73) Assignee: Novozymes A/S, Bagsvaerd (DK)

( * ) Notice: Subject to any disclaimer, the term of this patent is extended or adjusted under 35 U.S.C. 154(b) by 160 days.

This patent is subject to a terminal disclaimer.

(21) Appl. No.: 10/530,931

(22) PCT Filed: Oct. 10, 2003

(86) PCT No.: PCT/DK03/00684

§ 371 (c)(1),
(2), (4) Date: Jun. 14, 2005

(87) PCT Pub. No.: WO2004/032648

PCT Pub. Date: Apr. 22, 2004

(65) Prior Publication Data

US 2006/0275879 A1    Dec. 7, 2006

(30) Foreign Application Priority Data

Oct. 11, 2002    (DK)  .............................. 2002 01547

(51) Int. Cl.
C12N 9/82    (2006.01)
C12N 2/08    (2006.01)
A21D 2/00    (2006.01)
A23B 7/10    (2006.01)
C07H 21/04    (2006.01)
C07G 17/00    (2006.01)
C07K 1/00    (2006.01)

(52) U.S. Cl. ...................... 435/229; 435/189; 435/267; 435/272; 435/274; 426/20; 426/21; 426/48; 426/49; 426/52; 426/7; 536/23.2

(58) Field of Classification Search ........................ None
See application file for complete search history.

(56) References Cited

U.S. PATENT DOCUMENTS 5,310,670 A * 5/1994 Goward ...................... 435/229
6,039,982 A    3/2000 Wagner et al.
6,039,983 A    3/2000 Wagner et al.
2002/0004085 A1    1/2002 Xu et al.

FOREIGN PATENT DOCUMENTS

| EP | 0 963 704 | 12/1999 |
| WO | WO 94/28728 | * 12/1994 |
| WO | WO 96/39851 | 12/1996 |
| WO | WO 98/00029 | 1/1998 |
| WO | WO 99/57986 | 11/1999 |
| WO | WO 00/56762 | 9/2000 |
| WO | WO 02/30207 | 4/2002 |
| WO | WO 02/39828 | 5/2002 |

OTHER PUBLICATIONS

Tareke et al., Analysis of Acrylamide, a Carcinogen Formed in Heated Foodstuffs, Journal of Agricultural and Food Chemistry, vol. 50, pp. 4998-5006 (2002).
Mottram et al., Acrylamide is formed in the Maillard Reaction, Nature, vol. 419, pp. 448-449 (2002).
Biekman et al., VMT Voedingsmiddelentechnologie, vol. 22, No. 20, pp. 51-53 (1989).
Kim et al, Asparaginase II of *Saccharomyces cerevisiae*, Journal of Biological Chemistry, vol. 263, No. 24, pp. 11948-11953 (1988).
Abstract of JP 09009862 (Jan. 14, 1997).
Abstract of JP 10028516 ( Feb. 3, 1998).
Mohsen et al., Specificty of Lipase Produced by *Rhyzopus delemar* and Its Utilization in Bread Making, Egypt Journal Food Science, vol. 14, No. 1, pp. 175-182 (1986).
Marion et al., Wheat Lipids and Lipid-Binding Proteins: Structure and Function, published in Wheat Structure, Biochemistry and Functionality, The Proceedings of a Conference organized by the Royal Society of Chemistry Food Chemistry Group held in Reading UK, pp. 246-260 (Apr. 10-12, 1995).
Marion et al., Lipids, Lipid-Protein Interactions and the Quality of Baked Cereal Products, published in Interactions: The Keys to Cereal Quality, American Association of Cereal Chemists, pp. 130-167 (1998).
Poulsen et al., Effect and Functionality of Lipases in Dough and Bread, published in The first European Symposium on Enzymes and Grain Processing, pp. 204-214 (1996).

* cited by examiner

*Primary Examiner*—Rebecca E. Prouty
*Assistant Examiner*—Ganapathirama Raghu
(74) *Attorney, Agent, or Firm*—Elias J. Lambiris; Jason I. Garbell

(57) ABSTRACT

The formation of acrylamide during heat treatment in the production of a food product is reduced by treating the raw material with an enzyme before the heat treatment. The enzyme is capable of reacting on asparagine or glutamine (optionally substituted) as a substrate or is a laccase or a peroxidase.

27 Claims, No Drawings

ASPARAGINASES AND METHOD OF PREPARING A HEAT-TREATED PRODUCT

CROSS-REFERENCE TO RELATED APPLICATIONS

This application is a 35 U.S.C. 371 national application of PCT/DK2003/000684 filed Oct. 10, 2003, which claims priority or the benefit under 35 U.S.C. 119 of Danish application no. PA 2002 01547 filed Oct. 11, 2002 and U.S. provisional application no. 60/421,897 filed Oct. 29, 2002, the contents of which are fully incorporated herein by reference.

FIELD OF THE INVENTION

The present invention relates to a method of preparing a heat-treated product with a low water content from raw material comprising carbohydrate, protein and water. It also relates to an asparaginase for use in the method

BACKGROUND OF THE INVENTION

E. Tabeke et al. (*J. Agric. Food Chem.*, 2002, 50, 4998-5006) reported that acrylamide is formed during heating of starch-rich foods to high temperatures. The acrylamide formation has been ascribed to the Maillard reaction (D. S. Mottram et al., R. H. Stadtler et al., *Nature*, 419, 3 Oct. 2002, 448-449).

WO 00/56762 discloses expressed sequence tags (EST) from *A. oryzae*.

Kim, K.-W.; Kamerud, J. Q.; Livingston, D. M.; Roon, R. J., (1988) Asparaginase II of *Saccharomyces cerevisiae*. Characterization of the ASP3 gene. J. Biol. Chem. 263:11948, discloses the peptide sequence of an extra-cellular asparaginase

SUMMARY OF THE INVENTION

According to the invention, the formation of acrylamide during heat treatment of raw material comprising carbohydrate, protein and water is reduced by treating the raw material with an enzyme before the heat treatment. Accordingly, the invention provides a method of preparing a heat-treated product, comprising the sequential steps of:
a) providing a raw material which comprises carbohydrate, protein and water
b) treating the raw material with an enzyme, and
c) heat treating to reach a final water content below 35% by weight.

The enzyme is capable of reacting on asparagine or glutamine (optionally substituted) as a substrate or is a laccase or a peroxidase.

The invention also provides an asparaginase for use in the process and a polynucleotide encoding the asparaginase.

DETAILED DESCRIPTION OF THE INVENTION

Raw Material and Enzyme Treatment

The raw material comprises carbohydrate, protein and water, typically in amounts of 10-90% or 20-50% carbohydrate of the total weight. The carbohydrate may consist mainly of starch, and it may include reducing sugars such as glucose, e.g. added as glucose syrup, honey or dry dextrose. The protein may include free amino acids such as asparagine and glutamine (optionally substituted).

The raw material may include tubers, potatoes, grains, oats, barley, corn (maize), wheat, nuts, fruits, dried fruit, bananas, sesame, rye and/or rice.

The raw material may be in the form of a dough comprising finely divided ingredients (e.g. flour) with water. The enzyme treatment may be done by mixing (kneading) the enzyme into the dough and optionally holding to let the enzyme act. The enzyme may be added in the form of an aqueous solution, a powder, a granulate or agglomerated powder. The dough may be formed into desired shapes, e.g. by sheeting, cutting and/or extrusion.

The raw material may also be in the form of intact vegetable pieces, e.g. slices or other pieces of potato, fruit or bananas, whole nuts, whole grains etc. The enzyme treatment may comprise immersing the vegetable pieces in an aqueous enzyme solution and optionally applying vacuum infusion. The intact pieces may optionally be blanched by immersion in hot water, e.g. at 70-100° C., either before or after the enzyme treatment.

The raw material may be grain intended for malting, e.g. malting barley or wheat. The enzyme treatment of the grain may be done before, during or after the malting (germination).

The raw material before heat treatment typically has a water content of 10-90% by weight and is typically weakly acidic, e.g. having a pH of 5-7.

Heat Treatment

The process of the invention involves a heat treatment at high temperature to reach a final water content (moisture content) in the product below 35% by weight, typically 1-20%, 1-10% or 2-5%. During the heat treatment, the temperature at the surface of the product may reach 110-220° C., e.g. 110-170° C. or 120-160° C.

The heat treatment may involve, frying, particularly deep frying in tr- and/or di-glycerides (animal or vegetable oil or fat, optionally hydrogenated), e.g. at temperatures of 150-180° C. The heat treatment may also involve baking in hot air, e.g. at 160-310° C. or 200-250° C. for 2-10 minutes, or hot-plate heating. Further, the heat treatment may involve kilning of green malt.

Heat-Treated Product

The process of the invention may be used to produce a heat-treated product with low water content from raw material containing carbohydrate and protein, typically starchy food products fried or baked at high temperatures. The heat-treated product may be consumed directly as an edible product or may be used as an ingredient for further processing to prepare an edible or potable product.

Examples of products to be consumed directly are potato products, potato chips (crisps), French fries, hash browns, roast potatoes, breakfast cereals, crisp bread, muesli, biscuits, crackers, snack products, tortilla chips, roasted nuts, rice crackers (Japanese "senbei"), wafers, waffles, hot cakes, and pancakes.

Malt (e.g. caramelized malt or so-called chocolate malt) is generally further processed by mashing and brewing to make beer.

Enzyme Capable of Reacting with Asparagine or Glutamine (Optionally Substituted) as a Substrate The enzyme may be capable of reacting with asparagine or glutamine which is optionally glycosylated or substituted with a peptide at the alpha-amino and/or the carboxyl position. The enzyme may be an asparaginase, a glutaminase, an L-amino acid oxidase, a glycosylasparaginase, a glycoamidase or a peptidoglutaminase.

The glutaminase (EC 3.5.1.2) may be derived from *Escherichia coli*. The L-amino acid oxidase (EC 1.4.3.2) capable of reacting with asparagine or glutamine (optionally glycosylated) as a substrate may be derived from *Trichoderma harzianum* (WO 94/25574). The glycosylasparaginase (EC 3.5.1.26, aspartylglucosamimidase, N4-(N-acetyl-beta-glucosaminyl)-L-asparagine amidase) may be derived from *Flavobacterium meningosepticum*. The glycoamidase (peptide N-glycosidase, EC 3.5.1.52) may be derived from *Flavobactedium meningosepticum*. The peptidoglutaminase may be peptidoglutaminase I or II (EC 3.5.1.43, EC 3.5.1.44).

The enzyme is used in an amount which is effective to reduce the amount of acrylamide in the final product. The amount may be in the range 0.1-100 mg enzyme protein per kg dry matter, particularly 1-10 mg/kg. Asparaginase may be added in an amount of 10-100 units per kg dry matter where one unit will liberate 1 micromole of ammonia from L-asparagine per min at pH 8.6 at 37° C.

Asparaginase

The asparaginase (EC 3.5.1.1) may be derived from *Saccharomyces cerevisiae, Candia utilis, Escherichia coli, Aspergillus oryzae, Aspergillus nidulans, Aspergillus fumigatus, Fusarium graminearum*, or *Penicillium citrinum*. It may have the amino acid sequence shown in SEQ ID NO: 2 (optionally truncated to residues 27-378, 30-378, 75-378 or 80-378), 4, 6, 8, 10, 12 or 13 or a sequence which is at least 90% (particularly at least 95%) identical to one of these. It may be produced by use of the genetic information in SEQ ID NO: 1, 3, 5, 7, 9 or 11, e.g., as described in an example.

Whitehead Institute, MIT Center for Genome Research, Fungal Genome Initiative has published *A nidulans* release 1 and *F. graminearum* release 1 on the Internet at www-qenome.wi.mit.edu/ftp/distribution/annotation/under the *Aspergillus* Sequencing Project and the *Fusarium graminearum* Sequencing Project. Preliminary sequence data for *Aspergillus fumigatus* was published on The Institute for Genomic Research website at www-genome.wi.mit.edu/ftp/distribution/annotation/.

The inventors inserted the gene encoding the asparaginase from *A. oryzae* into *E. coli* and deposited the clone under the terms of the Budapest Treaty with the DSMZ—Deutsche Sammlung von Microorganismen und Zelikulturen GmbH, Mascheroder Weg 1b, D-38124 Braunschweig. The deposit number was DSM 15960, deposited on 6 Oct. 2003.

Alignment and Identity

The enzyme and the nucleotide sequence of the invention may have homologies to the disclosed sequences of at least 90% or at least 95%, e.g. at least 98%.

For purposes of the present invention, alignments of sequences and calculation of identity scores were done using a Needleman-Wunsch alignment (i.e. global alignment), useful for both protein and DNA alignments. The default scoring matrices BLOSUM50 and the identity matrix are used for protein and DNA alignments respectively. The penalty for the first residue in a gap is −12 for proteins and −16 for DNA, while the penalty for additional residues in a gap is −2 for proteins and −4 for DNA. Alignment is from the FASTA package version v20u6 (W. R. Pearson and D. J. Lipman (1988), "Improved Tools for Biological Sequence Analysis", PNAS 85:2444-2448, and W. R. Pearson (1990) "Rapid and Sensitive Sequence Comparison with FASTP and FASTA", Methods in Enzymology, 183:63-98).

Laccase or Peroxidase

The laccase (EC 1.10.3.2) may be of plant or microbial origin, e.g. from bacteria or fungi (including filamentous fungi and yeasts). Examples include laccase from *Aspergillus, Neurospora*, e.g., *N. crassa, Podospora, Botrytis, Collybia, Fomes, Lentinus, Pleurotus, Trametes*, e.g., *T. villosa* and *T. versicolor, Rhizoctonia*, e.g., *R. solani, Coprinus*, e.g., *C. cinereus, C. comatus, C. friesii*, and *C. plicatilis, Psathyrella*, e.g., *P. condelleana, Panaeolus*, e.g., *P. papilionaceus, Myceliophthora*, e.g., *M. thermophila, Schytalidium*, e.g., *S. thernophilum, Polyporus*, e.g., *P. pinsitus, Phlebia*, e.g., *P. radita*, or *Coriolus*, e.g., *C. hirsutus*.

The peroxidase (EC 1.11.1.7) may be from plants (e.g. horseradish or soybean peroxidase) or microorganisms such as fungi or bacteria, e.g. *Coprinus*, in particular *Coprinus cinereus f. microsporus* (IFO 8371), or *Coprinus macrorhizus, Pseudomonas*, e.g. *P. fluorescens* (NRRL B-11), *Streptoverticillium*, e.g. *S. verticillium* ssp. *verticillium* (IFO 13864), *Streptomyces*, e.g. *S. thermoviolaceus* (CBS 278.66), *Streptomyces*, e.g. *S. viridosporus* (ATCC 39115), *S. badius* (ATCC 39117), *S. phaeochromogenes* (NRRL B-3559), *Pseudomonas*, e.g. *P. pyrrocinia* (ATCC 15958), *Fusarium*, e.g. *F. oxysporum* (DSM 2672) and *Bacillus*, e.g. *B. stearothermophilus* (ATCC 12978).

Oxidoreductase Capable of Reacting with a Reducing Sugar as a Substrate

The method of the invention may comprise treating the raw material with an oxidoreductase capable of reacting with a reducing sugar as a substrate. The oxidoreductase may be an oxidase or dehydrogenase capable of reacting with a reducing sugar as a substrate such as glucose and maltose.

The oxidase may be a glucose oxidase, a pyranose oxidase, a hexose oxidase, a galactose oxidase (EC 1.1.3.9) or a carbohydrate oxidase which has a higher activity on maltose than on glucose. The glucose oxidase (EC 1.1.3.4) may be derived from *Aspergillus niger* e.g. having the amino acid sequence described in U.S. Pat. No. 5,094,951. The hexose oxidase (EC 1.1.3.5) may be derived from algal species such as *Irdophycus flaccidum, Chondrus crispus* and *Euthora cristata*. The pyranose oxidase may be derived from *Basidiomycete* fungi, *Peniophora gigantean, Aphyllophorales, Phanerochaete chrysosporium, Polyporus pinsitus, Bierkandera adusta* or *Phlebiopsis gigantean*. The carbohydrate oxidase which has a higher activity on maltose than on glucose may be derived from *Microdochium* or *Acremonium*, e.g. from *M. nivale* (U.S. Pat. No. 6,165,761), *A. strictum, A. fusidioides* or *A. potronii*.

The dehydrogenase may be glucose dehydrogenase (EC 1.1.1.47, EC 1.1.99.10), galactose dehydrogenase (EC 1.1.1.48), D-aldohexose dehydrogenase (EC 1.1.1.118, EC 1.1.1.119), cellobiose dehydrogenase (EC 1.1.5.1, e.g. from *Humicola insolens*), fructose dehydrogenase (EC 1.1.99.11, EC 1.1.1.124, EC 1.1.99.11), aldehyde dehydrogenase (EC 1.2.1.3, EC 1.2.1.4, EC 1.2.1.5). Another example is glucose-fructose oxidoreductase (EC 1.1.99.28).

The oxidoreductase is used in an amount which is effective to reduce the amount of acrylamide in the final product. For glucose oxidase, the amount may be in the range 50-20,000 (e.g. 100-10,000 or 1,000-5,000) GODU/kg dry matter in the raw material. One GODU is the amount of enzyme which forms 1 μmol of hydrogen peroxide per minute at 30° C., pH 5.6 (acetate buffer) with glucose 16.2 g/l (90 mM) as substrate using 20 min. incubation time. For other enzymes, the dosage may be found similarly by analyzing with the appropriate substrate.

EXAMPLES

Media

DAP2C-1
    11 g $MgSO_4.7H_2O$
    1 g $KH_2PO_4$
    2 g Citric acid, monohydrate
    30 g maltodextrin
    6 g $K_3PO_4.3H_2O$
    0.5 g yeast extract
    0.5 ml trace metals solution
    1 ml Pluronic PE 6100 (BASF, Ludwigshafen, Germany)

Components are blended in one liter distilled water and portioned out to flasks, adding 250 mg CaCO3 to each 150 ml portion.

The medium is sterilized in an autoclave. After cooling the following is added to 1 liter of medium:
    23 ml 50% w/v $(NH_4)_2HPO_4$, filter sterilized
    33 ml 20% lactic acid, filter sterilized Trace Metals Solution
    6.8 g $ZnCl_2$
    2.5 g $CuSO_4.5H_2O$
    0.24 g $NiCl_2.6H_2O$
    13.9 g $FeSO_4.7H_2O$
    8.45 g $MnSO_4.H_2O$
    3 g Citric acid, monohydrate Components are blended in one liter distilled water.

Asparaginase Activity Assay

Stock Solutions
    50 mM Tris buffer, pH 8.6
    189 mM L-Asparagine solution
    1.5 M Trichloroacetic Acid (TCA)
    Nessler's reagent, Aldrich Stock No. 34,514-8 (Sigma-Aldrich, St. Louis, Mo. USA)
    Asparaginase, Sigma Stock No. A4887 (Sigma-Aldrich, St. Louis, Mo. USA)

Assay

Enzyme Reaction:
    500 micro-I buffer
    100 micro-I L-asparagine solution
    350 micro-I water
    are mixed and equilibrated to 37° C.

100 micro-I of enzyme solution is added and the reactions are incubated at 37° C. for 30 minutes.

The reactions are stopped by placing on ice and adding 50 micro-I of 1.5M TCA.

The samples are mixed and centrifuged for 2 minutes at 20,000 g

Measurement of Free Ammonium:
    50 micro-I of the enzyme reaction is mixed with 100 micro-I of water and 50 micro-I of Nessler's reagent. The reaction is mixed and absorbance at 436 nm is measured after 1 minute.

Standard:
    The asparaginase stock (Sigma A4887) is diluted 0.2, 0.5, 1, 1.5, 2, and 2.5 U/ml.

Example 1

Expression of an Asparaginase from *Aspergillus oryzae* in *Aspergillus otyzae*

Libraries of cDNA of mRNA from *Aspergillus otyzae* were generated, sequenced and stored in a computer database as described in WO 00/56762.

The peptide sequence of asparaginase II from *Saccharomyces cerevisiae* (Kim, K.-W.; Kamerud, J. Q.; Livingston, D. M.; Roon, R. J., (1988) Asparaginase II of *Saccharomyces cerevisiae*. Characterization of the ASP3 gene. J. Biol. Chem. 263:11948), was compared to translations of the *Aspergillus oryzae* partial cDNA sequences using the TFASTXY program, version 3.2t07 (Pearson et al, Genomics (1997) 46:24-36). One translated *A. oryzae* sequence was identified as having 52% identity to yeast asparaginase II through a 165 amino acid overlap. The complete sequence of the cDNA insert of the corresponding clone (deposited as DSM 15960) was determined and is presented as SEQ ID NO: 1, and the peptide translated from this sequence, AoASP, is presented as SEQ ID NO: 2. This sequence was used to design primers for PCR amplification of the AoASP encoding-gene from DSM 15960, with appropriate restriction sites added to the primer ends to facilitate sub-cloning of the PCR product (primers AoASP7 and AoASP8, SEQ ID NOS: 14 and 15). PCR amplification was performed using Extensor Hi-Fidelity PCR Master Mix (ABgene, Surrey, U.K.) following the manufacturer's instructions and using an annealing temperature of 55° C. for the first 5 cycles and 65° C. for an additional 30 cycles and an extension time of 1.5 minutes.

The PCR fragment was restricted with BamHI and HindIII and cloned into the *Aspergillus* expression vector pMStr57 using standard techniques. The expression vector pMStr57 contains the same elements as pCaHj483 (WO 98/00529), with minor modifications made to the *Aspergillus* NA2 promoter as described for the vector pMT2188 in WO 01/12794, and has sequences for selection and propogation in *E. coli*, and selection and expression in *Aspergillus*. Specifically, selection in *Aspergillus* is facilitated by the amdS gene of *Aspergillus nidulans*, which allows the use of acetamide as a sole nitrogen source. Expression in *Aspergillus* is mediated by a modified neutral amylase II (NA2) promoter from *Aspergillus niger* which is fused to the 5' leader sequence of the triose phosphate isomerase (tpi) encoding-gene from *Aspergillus nidulans*, and the terminator from the amyloglucosidase-encoding gene from *Aspergillus niger*. The asparaginase-encoding gene of the resulting *Aspergillus* expression construct, pMStr90, was sequenced and the sequence agreed completely with that determined previously for the insert of DSM 15960

The *Aspergillus oryzae* strain BECh2 (WO 00/39322) was transformed with pMStr90 using standard techniques (Christensen, T. et al., (1988), Biotechnology 6, 1419-1422). Transformants were cultured in DAP2C-1 medium shaken at 200 RPM at 30° C. and expression of AoASP was monitored by SDS-PAGE and by measuring enzyme activity.

Example 2

Purification of Asparaginase

Culture broth from the preceding example was centrifuged (20000×g, 20 min) and the supernatants were carefully decanted from the precipitates. The combined supernatants were filtered through a Seitz EKS plate in order to remove the rest of the *Aspergillus* host cells. The EKS filtrate was transferred to 10 mM Tris/HCl, pH 8 on a G25 sephadex column and applied to a Q sepharose HP column equilibrated in the same buffer. After washing the Q sepharose HP column extensively with the equilibration buffer, the asparaginase was eluted with a linear NaCl gradient (0–>0.5M) in the same buffer. Fractions from the column were analysed for asparaginase activity (using the pH 6.0 Universal buffer) and fractions with activity were pooled. Ammonium sulfate was added to the pool to 2.0M final concentration and the pool was applied to a Phenyl Toyopearl S column equilibrated in 20 mM succinic acid, 2.0M $(NH_4)_2SO_4$, pH 6.0. After washing the Phenyl column extensively with the equilibration buffer, the enzyme was eluted with a linear $(NH_4)_2SO_4$ gradient (2.0–>0M) in the same buffer. Fractions from the column were again analysed for asparaginase activity and active fractions were further analysed by SDS-PAGE. Fractions, which was judged only to contain the asparaginase, were pooled as the purified preparation and was used for further characterization. The purified asparaginase was heterogeneously glycosylated judged from the coomassie stained SDS-PAGE gel and in addition N-terminal sequencing of the preparation revealed that the preparation contained different asparaginase forms, as four different N-termini were found starting at amino acids $A_{27}$, $S_{30}$, $G_{75}$ and $A_{80}$ respectively of SEQ ID NO: 2. However, the N-terminal sequencing also indicated that the purified preparation was relatively pure as no other N-terminal sequences were found by the analysis.

Example 3

Properties of Asparaginase

The purified asparaginase from the preceding example was used for characterization.

Asparaginase Assay

A coupled enzyme assay was used. Asparaginase was incubated with asparagine and the liberated ammonia was determined with an Ammonia kit from Boehringer Mannheim (cat. no. 1 112 732) based on glutamate dehydrogenase and NADH oxidation to $NAD^+$ (can be measured as a decrease in $A_{375}$). Hence the decrease in absorbance at 375 nm was taken as a measure of asparaginase activity.

| | |
|---|---|
| Asparagine substrate: | 10 mg/ml L-asparagine (Sigma A-7094) was dissolved in Universal buffers and pH was adjusted to the indicated pH-values with HCl or NaOH. |
| Temperature: | controlled |
| Universal buffers: | 100 mM succinic acid, 100 mM HEPES, 100 mM CHES, 100 mM CABS, 1 mM $CaCl_2$, 150 mM KCl, 0.01% Triton X-100 adjusted to pH-values 2.0, 3.0, 4.0, 5.0, 6.0, 7.0, 8.0, 9.0, 10.0, 11.0 and 12.0 with HCl or NaOH. |
| Stop reagent: | 500 mM TCA (Trichloroacetic acid). |
| Assay buffer: | 1.0M $KH_2PO_4$/NaOH, pH 7.5. |
| Ammonia reagent A: | 1 NADH tablet + 1.0 ml Bottle 1 (contain 2-oxoglutarate (second substrate) and buffer) + 2.0 ml Assay buffer. |
| Ammonia reagent B: | 40 micro-l Bottle 3 (contain glutamate dehydrogenase) + 1460 micro-l Assay buffer. |

450 micro-I asparagine substrate was placed on ice in an Eppendorf tube. 50 micro-I asparaginase sample (diluted in 0.01% Triton X-100) was added. The assay was initiated by transferring the Eppendorf tube to an Eppendorf thermomixer, which was set to the assay temperature. The tube was incubated for 15 minutes on the Eppendorf thermomixer at its highest shaking rate (1400 rpm). The incubation was stopped by transferring the tube back to the ice bath and adding 500 micro-I Stop reagent. The tube was vortexed and centrifuged shortly in an icecold centrifuge to precipitate the proteins in the tube. The amount of ammonia liberated by the enzyme was measured by the following procedure: 20 micro-I supernatant was transferred to a microtiter plate, 200 micro-I Ammonia reagent A was added and A375 was read ($A_{375}$ (initial)). Then 50 micro-I Ammonia reagent B was added and after 10 minutes at room temperature the plate was read again ($A_{375}$(final)). $A_{375}$(initial)–$A_{375}$(final) was a measure of asparaginase activity. A buffer blind was included in the assay (instead of enzyme) and the decrease in $A_{375}$ in the buffer blind was subtracted from the enzyme samples.

pH-activity, pH-stability, and Temperature-activity of Asparaginase

The above asparaginase assay was used for obtaining the pH-activity profile, the pH-stability profile as well as the temperature-activity profile at pH 7.0. For the pH-stability profile the asparaginase was diluted 7× in the Universal buffers and incubated for 2 hours at 37° C.

After incubation the asparaginase samples were transferred to neutral pH, before assay for residual activity, by dilution in the pH 7 Universal buffer.

The results for the: pH-activity profile at 37° C. were as follows, relative to the residual activity at after 2 hours at pH 7.0 and 5° C.:

| pH | Asparaginase |
|---|---|
| 2 | 0.00 |
| 3 | 0.01 |
| 4 | 0.10 |
| 5 | 0.53 |
| 6 | 0.95 |
| 7 | 1.00 |
| 8 | 0.66 |
| 9 | 0.22 |
| 10 | 0.08 |
| 11 | 0.00 |

The results for the pH-stability profile (residual activity after 2 hours at 37° C.) were as follows:

| pH | Asparaginase |
|---|---|
| 2.0 | 0.00 |
| 3.0 | 0.00 |
| 4.0 | 1.06 |
| 5.0 | 1.08 |
| 6.0 | 1.09 |
| 7.0 | 1.09 |
| 8.0 | 0.92 |
| 9.0 | 0.00 |
| 10.0 | 0.00 |
| 11.0 | 0.00 |
| 12.0 | 0.00 |
| | 1.00 |

The results for the temperature activity profile (at pH 7.0) were as follows:

| Temp (° C.) | Asparaginase |
|---|---|
| 15 | 0.24 |
| 25 | 0.39 |
| 37 | 0.60 |
| 50 | 0.81 |
| 60 | 1.00 |
| 70 | 0.18 |

Other Characteristics

The relative molecular weight as determined by SDS-PAGE was seen as a broad band (a smear) at $M_r$=40-65 kDa.

N-terminal sequencing showed four different terminals, corresponding to residues 27-37, 30-40, 75-85 and 80-91 of SEQ ID NO: 2, respectively.

Example 3

Cloning of Asparaginase from *Penicilium citrinum*

*Penicillium citrinum* was grown in MEX-1 medium (Medium B in WO 98/38288) in flask shaken at 150 RPM at 26° C. for 3 and 4 days. Mycelium was harvested, a cDNA library constructed, and cDNAs encoding secreted peptides were selected and sequenced by the methods described in WO 03/044049. Comparison to known sequences by methods described in WO 03/044049 indicated that *Penicillium* sequence ZY132299 encoded an asparaginase. The complete sequence of the corresponding cDNA was determined and is presented ss SEQ ID NO: 11, and the peptide translated from this sequence is presented as SEQ ID NO: 12.

Example 4

Effect of Asparaginase on Acrylamide Content in Potato Chips

Asparaginase from *A. oryzae* having the amino acid sequence shown in SEQ ID NO: 2 was prepared and purified as in Examples 1-2 and added at various dosages to potato chips made from 40 g of water, 52.2 g of dehydrated potato flakes, 5.8 g of potato starch and 2 g of salt.

The flour and dry ingredients were mixed for 30 sec. The salt and enzyme were dissolved in the water, and the solution was adjusted to 30° C. The solution was added to the flour. The dough was further mixed for 15 min. The mixed dough was placed in a closed plastic bag and allowed to rest for 15 min at room temperature.

The dough was then Initially compressed for 60 sec in a dough press.

The dough was sheeted and folded in a noodle roller machine until an approx. 5-10 mm dough is obtained. The dough was then rolled around a rolling pin and allowed to rest for 30 min in a plastic bag at room temperature. The dough was sheeted further to a final sheet thickness of approx 1.2 mm.

The sheet was cut into squares of approx 3×5 cm.

The sheets were placed in a frying basket, placed in an oil bath and fried for 45 sec at 180° C. The noodle basket was held at a 45° angle until the oil stopped dripping. The products were removed from the basket and left to cool on dry absorbent paper.

The potato chips were homogenized and analyzed for acrylamide. The results were as follows:

| Asparaginase dosage U/kg potato dry matter | Acrylamide Micro-g per kg |
|---|---|
| 0 | 5,200 |
| 100 | 4,600 |
| 500 | 3,100 |
| 1000 | 1,200 |
| 2000 | 150 |

The results demonstrate that the asparaginase treatment is effective to reduce the acrylamide content in potato chips, that the acrylamide reduction is clearly dosage dependent, and that the acrylamide content can be reduced to a very low level.

Example 5

Effect of Various Enzymes on Acrylamide Content in Potato Chips

Potato chips were made as follows with addition of enzyme systems which are capable of reacting on asparagine, as indicated below.

Recipe:

| | |
|---|---|
| Tap water | 40 g |
| Potato flakes dehydrated | 52.2 g |
| Potato starch | 5.8 g |
| Salt | 2 g |

Dough Procedure:

The potato and potato starch are mixed for 30 sec in a mixer at speed 5. Salt and enzyme are dissolved in the water. The solution is adjusted to 30° C.+/−1° C. Stop mixer, add all of the salt/enzyme solution to flour. The dough is further mixed for 15 min.

Place mixed dough in plastic bag, close bag and allow the dough to rest for 15 min at room temperature.

The dough is then initially compressed for 60 sec in a dough press.

The dough is sheeted and folded in a noodle roller machine until an approx. 5-10 mm dough is obtained. The dough is then rolled around a rolling pin and the dough is allowed to rest for 30 min in a plastic bag at room temperature. The dough is sheeted further to a final sheet thickness of approx 1.2 mm.

Cut the sheet into squares of approx 3×5 cm.

Sheets are placed in a frying basket, placed in the oil bath and fried for 60 sec at 180° C. Hold the noodle basket at a 45° angle and let the product drain until oil stops dripping. Remove the products from the basket and leave them to cool on dry absorbent paper.

The results from acrylamide analysis were as follows:

| Enzyme | Enzyme dosage per kg of potato dry matter | Acrylamide Micro-g per kg |
|---|---|---|
| None (control) | 0 | 4,100 |
| Asparaginase from | 1000 U/kg | 150 |

| Enzyme | Enzyme dosage per kg of potato dry matter | Acrylamide Micro-g per kg |
|---|---|---|
| *Erwinia Chrysanthemi* A-2925 | 50 mg enzyme protein/kg | 1,800 |
| Glutaminase (product of Daiwa) | 50 mg enzyme protein/kg | 1,300 |
| Amino acid oxidase from *Trichoderma harzianum* described in WO 9425574. | | |
| Laccase from *Myceliophthora thermophila* + peroxidase from *Coprinus* | 5000 LAMU/kg + 75 mg enzyme protein/kg | 2,000 |

The results demonstrate that all the tested enzyme systems are effective in reducing the acrylamide content of potato chips.

---

SEQUENCE LISTING

<160> NUMBER OF SEQ ID NOS: 15

<210> SEQ ID NO 1
<211> LENGTH: 1303
<212> TYPE: DNA
<213> ORGANISM: Aspergillus oryzae
<220> FEATURE:
<221> NAME/KEY: CDS
<222> LOCATION: (49)..(1182)

<400> SEQUENCE: 1

```
ccacgcgtcc gattccctac tcagagcccc gagcaaccaa gcagcagt atg ggt gtc      57
                                                   Met Gly Val
                                                     1 aat ttc aaa gtt ctt gcc ctg tcg gcc tta gct act att agc cat gct    105
Asn Phe Lys Val Leu Ala Leu Ser Ala Leu Ala Thr Ile Ser His Ala
  5                  10                  15 tcg cct ctc cta tat cct cga gcc aca gac tcg aac gtc acc tat gtg    153
Ser Pro Leu Leu Tyr Pro Arg Ala Thr Asp Ser Asn Val Thr Tyr Val
 20                  25                  30                  35 ttc acc aac ccc aat ggc ctg aac ttt act cag atg aac acc acc ctg    201
Phe Thr Asn Pro Asn Gly Leu Asn Phe Thr Gln Met Asn Thr Thr Leu
             40                  45                  50 cca aac gtc act atc ttc gcg aca ggc ggc aca atc gcg ggc tcc agc    249
Pro Asn Val Thr Ile Phe Ala Thr Gly Gly Thr Ile Ala Gly Ser Ser
         55                  60                  65 gcc gac aac acc gca aca aca ggt tac aaa gcc ggt gca gtc ggc atc    297
Ala Asp Asn Thr Ala Thr Thr Gly Tyr Lys Ala Gly Ala Val Gly Ile
     70                  75                  80 cag aca ctg atc gac gcg gtc ccg gaa atg cta aac gtt gcc aac gtc    345
Gln Thr Leu Ile Asp Ala Val Pro Glu Met Leu Asn Val Ala Asn Val
 85                  90                  95 gct ggc gtg caa gta acc aat gtc ggc agc cca gac atc acc tcc gac    393
Ala Gly Val Gln Val Thr Asn Val Gly Ser Pro Asp Ile Thr Ser Asp
100                 105                 110                 115 att ctc ctg cgt ctc tcc aaa cag atc aac gag gtg gtc tgc aac gac    441
Ile Leu Leu Arg Leu Ser Lys Gln Ile Asn Glu Val Val Cys Asn Asp
             120                 125                 130 ccc acc atg gcc ggt gca gtg gtc acc cac ggc acc gac acg ctc gaa    489
Pro Thr Met Ala Gly Ala Val Val Thr His Gly Thr Asp Thr Leu Glu
         135                 140                 145 gaa tcc gcc ttc ttc ctc gac gcc acg gtc aac tgt cgc aag ccc gtg    537
Glu Ser Ala Phe Phe Leu Asp Ala Thr Val Asn Cys Arg Lys Pro Val
     150                 155                 160 gtc atc gtc ggc gcc atg cgc cct tca acc gcc atc tcg gct gac ggc    585
Val Ile Val Gly Ala Met Arg Pro Ser Thr Ala Ile Ser Ala Asp Gly
```

```
                                  -continued 165                  170                  175
ccc ctc aac ctc ctg caa tcc gtc acc gtc gcc gcg agc ccc aag gcc      633
Pro Leu Asn Leu Leu Gln Ser Val Thr Val Ala Ala Ser Pro Lys Ala
180                 185                 190                 195 cga gac cgc ggc gcc ctg att gtc atg aac gac cgc atc gta tcc gcc      681
Arg Asp Arg Gly Ala Leu Ile Val Met Asn Asp Arg Ile Val Ser Ala
                    200                 205                 210 ttc tac gcc tcc aag acg aac gcc aac acc gtc gat aca ttc aag gcc      729
Phe Tyr Ala Ser Lys Thr Asn Ala Asn Thr Val Asp Thr Phe Lys Ala
            215                 220                 225 atc gaa atg ggt aac ctg ggc gag gtc gtc tcc aac aaa ccc tac ttc      777
Ile Glu Met Gly Asn Leu Gly Glu Val Val Ser Asn Lys Pro Tyr Phe
        230                 235                 240 ttc tac ccc cca gtc aag cca aca ggc aag acg gaa gta gat atc cgg      825
Phe Tyr Pro Pro Val Lys Pro Thr Gly Lys Thr Glu Val Asp Ile Arg
    245                 250                 255 aac atc acc tcc atc ccc aga gtc gac atc ctc tac tca tac gaa gac      873
Asn Ile Thr Ser Ile Pro Arg Val Asp Ile Leu Tyr Ser Tyr Glu Asp
260                 265                 270                 275 atg cac aat gac acc ctt tac tcc gcc atc gac aac ggc gca aag ggc      921
Met His Asn Asp Thr Leu Tyr Ser Ala Ile Asp Asn Gly Ala Lys Gly
                    280                 285                 290 atc gtt atc gcc ggc tcc ggc tcc ggc tcc gtc tcc acc ccc ttc agc      969
Ile Val Ile Ala Gly Ser Gly Ser Gly Ser Val Ser Thr Pro Phe Ser
            295                 300                 305 gcc gcc atg gaa gac atc aca acc aaa cac aac atc ccc atc gta gcc     1017
Ala Ala Met Glu Asp Ile Thr Thr Lys His Asn Ile Pro Ile Val Ala
        310                 315                 320 agc acg cgc acc gga aac ggg gag gtg ccg tcc tcc gcc gag tcg agc     1065
Ser Thr Arg Thr Gly Asn Gly Glu Val Pro Ser Ser Ala Glu Ser Ser
    325                 330                 335 cag atc gca agc ggg tat ttg aac ccc gca aag tca cgc gtt ttg ctt     1113
Gln Ile Ala Ser Gly Tyr Leu Asn Pro Ala Lys Ser Arg Val Leu Leu
340                 345                 350                 355 ggc ttg ttg ctt gcc cag ggg aag agt att gag gaa atg agg gcg gtt     1161
Gly Leu Leu Leu Ala Gln Gly Lys Ser Ile Glu Glu Met Arg Ala Val
                    360                 365                 370 ttt gag cgg att ggg gtt gct tgatttttt ttcttttctg cttggtcttt          1212
Phe Glu Arg Ile Gly Val Ala
            375 gtttagggtt ggggtttgtg tattatagat taaggattta tggatgggat ggataataga   1272 ttatagatta tagattaagt atcgattatg g                                   1303

<210> SEQ ID NO 2
<211> LENGTH: 378
<212> TYPE: PRT
<213> ORGANISM: Aspergillus oryzae

<400> SEQUENCE: 2

Met Gly Val Asn Phe Lys Val Leu Ala Leu Ser Ala Leu Ala Thr Ile
1               5                   10                  15

Ser His Ala Ser Pro Leu Leu Tyr Pro Arg Ala Thr Asp Ser Asn Val
            20                  25                  30

Thr Tyr Val Phe Thr Asn Pro Asn Gly Leu Asn Phe Thr Gln Met Asn
        35                  40                  45

Thr Thr Leu Pro Asn Val Thr Ile Phe Ala Thr Gly Gly Thr Ile Ala
    50                  55                  60

Gly Ser Ser Ala Asp Asn Thr Ala Thr Thr Gly Tyr Lys Ala Gly Ala
```

```
                65                  70                  75                  80
Val Gly Ile Gln Thr Leu Ile Asp Ala Val Pro Glu Met Leu Asn Val
                    85                  90                  95
Ala Asn Val Ala Gly Val Gln Val Thr Asn Val Gly Ser Pro Asp Ile
                100                 105                 110
Thr Ser Asp Ile Leu Leu Arg Leu Ser Lys Gln Ile Asn Glu Val Val
                115                 120                 125
Cys Asn Asp Pro Thr Met Ala Gly Ala Val Val Thr His Gly Thr Asp
            130                 135                 140
Thr Leu Glu Glu Ser Ala Phe Phe Leu Asp Ala Thr Val Asn Cys Arg
145                 150                 155                 160
Lys Pro Val Val Ile Val Gly Ala Met Arg Pro Ser Thr Ala Ile Ser
                165                 170                 175
Ala Asp Gly Pro Leu Asn Leu Leu Gln Ser Val Thr Val Ala Ala Ser
                180                 185                 190
Pro Lys Ala Arg Asp Arg Gly Ala Leu Ile Val Met Asn Asp Arg Ile
                195                 200                 205
Val Ser Ala Phe Tyr Ala Ser Lys Thr Asn Ala Asn Thr Val Asp Thr
    210                 215                 220
Phe Lys Ala Ile Glu Met Gly Asn Leu Gly Glu Val Val Ser Asn Lys
225                 230                 235                 240
Pro Tyr Phe Phe Tyr Pro Pro Val Lys Pro Thr Gly Lys Thr Glu Val
                245                 250                 255
Asp Ile Arg Asn Ile Thr Ser Ile Pro Arg Val Asp Ile Leu Tyr Ser
                260                 265                 270
Tyr Glu Asp Met His Asn Asp Thr Leu Tyr Ser Ala Ile Asp Asn Gly
    275                 280                 285
Ala Lys Gly Ile Val Ile Ala Gly Ser Gly Ser Gly Ser Val Ser Thr
    290                 295                 300
Pro Phe Ser Ala Ala Met Glu Asp Ile Thr Thr Lys His Asn Ile Pro
305                 310                 315                 320
Ile Val Ala Ser Thr Arg Thr Gly Asn Gly Glu Val Pro Ser Ser Ala
                325                 330                 335
Glu Ser Ser Gln Ile Ala Ser Gly Tyr Leu Asn Pro Ala Lys Ser Arg
                340                 345                 350
Val Leu Leu Gly Leu Leu Leu Ala Gln Gly Lys Ser Ile Glu Glu Met
        355                 360                 365
Arg Ala Val Phe Glu Arg Ile Gly Val Ala
    370                 375

<210> SEQ ID NO 3
<211> LENGTH: 1400
<212> TYPE: DNA
<213> ORGANISM: Aspergillus nidulans
<220> FEATURE:
<221> NAME/KEY: CDS
<222> LOCATION: (89)..(269)
<220> FEATURE:
<221> NAME/KEY: CDS
<222> LOCATION: (347)..(1299)

<400> SEQUENCE: 3 cccttatga cggccgaaag atggatatgc tactatacag attcagcctt cttgcctttg      60
ggagagcgtt tgatactata cgcaaatc atg ggt ctc cgt gtc aaa gcc ctt      112
                                Met Gly Leu Arg Val Lys Ala Leu
                                  1               5
```

```
gca gtg gca gct ctg gct acc ctc agc cag gcc tcg ccg gtc cta tac      160
Ala Val Ala Ala Leu Ala Thr Leu Ser Gln Ala Ser Pro Val Leu Tyr
     10              15                  20 act cgc gag gac act acc tcc aac aca acc tac gcc ttt acc aac agc      208
Thr Arg Glu Asp Thr Thr Ser Asn Thr Thr Tyr Ala Phe Thr Asn Ser
 25              30                  35                  40 aac ggg ctg aac ttc acc cag atg aac acc aca ctt cct aat gta acc      256
Asn Gly Leu Asn Phe Thr Gln Met Asn Thr Thr Leu Pro Asn Val Thr
                 45                  50                  55 atc ttc gca aca g gtatgaccgt cccttcactt tcccatctct ttccaacccc        309
Ile Phe Ala Thr
         60 cttcagcaaa cagcaaacta aacaatagca acaacag gc  ggc aca atc gcc ggc     363
                                            Gly Gly Thr Ile Ala Gly
                                                                 65 tcg gcc gcc tct aac act gca aca aca ggc tac cag gcg ggc gcc ctc      411
Ser Ala Ala Ser Asn Thr Ala Thr Thr Gly Tyr Gln Ala Gly Ala Leu
             70                  75                  80 gga atc cag acc ctc atc gac gcc gtc ccc gaa atg ctc tcc gtc gcc      459
Gly Ile Gln Thr Leu Ile Asp Ala Val Pro Glu Met Leu Ser Val Ala
         85                  90                  95 aac atc gcc ggc gtg cag atc tcc aac gtc ggt agc cca gac gtc acc      507
Asn Ile Ala Gly Val Gln Ile Ser Asn Val Gly Ser Pro Asp Val Thr
     100                 105                 110 tcc acc atc ctg cta gag atg gcg cac cgt ctc aac aaa gtt gtc tgc      555
Ser Thr Ile Leu Leu Glu Met Ala His Arg Leu Asn Lys Val Val Cys
115                 120                 125                 130 gag gac cca tcc atg gct ggc gca gtc gtc acc cac ggc act gac acc      603
Glu Asp Pro Ser Met Ala Gly Ala Val Val Thr His Gly Thr Asp Thr
                 135                 140                 145 ctt gag gaa acg gcc ttc ttc ctc gac gca aca gtc aac tgc ggg aag      651
Leu Glu Glu Thr Ala Phe Phe Leu Asp Ala Thr Val Asn Cys Gly Lys
             150                 155                 160 cct att gtc atc gtg ggc gcc atg cgg ccc gca aca ttc atc tct gcc      699
Pro Ile Val Ile Val Gly Ala Met Arg Pro Ala Thr Phe Ile Ser Ala
         165                 170                 175 gat ggg ccc tat aat ctc ctg cag gcc gtt act gtg gcg agc acg aaa      747
Asp Gly Pro Tyr Asn Leu Leu Gln Ala Val Thr Val Ala Ser Thr Lys
     180                 185                 190 gag gca agg aac agg ggc gcg atg gtc gtc atg aac gac cgc atc gcc      795
Glu Ala Arg Asn Arg Gly Ala Met Val Val Met Asn Asp Arg Ile Ala
195                 200                 205                 210 tcc gct tac tac gtg tcc aag aca aac gcc aat acg atg gat aca ttc      843
Ser Ala Tyr Tyr Val Ser Lys Thr Asn Ala Asn Thr Met Asp Thr Phe
                 215                 220                 225 aag gct gtg gaa atg ggg tac ctg ggt gcc att atc tcg aac act ccg      891
Lys Ala Val Glu Met Gly Tyr Leu Gly Ala Ile Ile Ser Asn Thr Pro
             230                 235                 240 ttc ttc tat tac ccg gcc gtg cag cca agt ggg aag acg act gtc gat      939
Phe Phe Tyr Tyr Pro Ala Val Gln Pro Ser Gly Lys Thr Thr Val Asp
         245                 250                 255 gtg tcc aac gtc acc tcc atc ccg cgc gtc gac atc ctc tac tcc ttc      987
Val Ser Asn Val Thr Ser Ile Pro Arg Val Asp Ile Leu Tyr Ser Phe
     260                 265                 270 cag gac atg aca aac gac acg ctc tac tca agc att gag aac ggc gcg     1035
Gln Asp Met Thr Asn Asp Thr Leu Tyr Ser Ser Ile Glu Asn Gly Ala
275                 280                 285                 290 aag ggc gtt gtt atc gca gga tct ggt gct ggg agt gtc gat acc gcc     1083
Lys Gly Val Val Ile Ala Gly Ser Gly Ala Gly Ser Val Asp Thr Ala
                 295                 300                 305
```

```
ttc tcg acg gct att gat gat att atc agc aac cag gga gtt ccg atc    1131
Phe Ser Thr Ala Ile Asp Asp Ile Ile Ser Asn Gln Gly Val Pro Ile
            310                 315                 320 gtg cag agt act agg aca gga aac gga gag gtg ccg tat tcg gct gag    1179
Val Gln Ser Thr Arg Thr Gly Asn Gly Glu Val Pro Tyr Ser Ala Glu
        325                 330                 335 ggg ggt att tcg agc ggg ttc ctg aac cca gct aag tcg agg att ttg    1227
Gly Gly Ile Ser Ser Gly Phe Leu Asn Pro Ala Lys Ser Arg Ile Leu
    340                 345                 350 ttg gga ttg ctg ttg gcc cag gga ggg aag ggc act gaa gaa att agg    1275
Leu Gly Leu Leu Leu Ala Gln Gly Gly Lys Gly Thr Glu Glu Ile Arg
355                 360                 365                 370 gcg gtg ttt ggg aag gtt gct gtt tgattcccga ctgcccaggg cttatgatgt   1329
Ala Val Phe Gly Lys Val Ala Val
                375 gatttgatga gatatggtat aataatccgt atatatccag tagatatcat ggaagatgat  1389 gaatagctgc c                                                        1400

<210> SEQ ID NO 4
<211> LENGTH: 378
<212> TYPE: PRT
<213> ORGANISM: Aspergillus nidulans

<400> SEQUENCE: 4

Met Gly Leu Arg Val Lys Ala Leu Ala Val Ala Ala Leu Ala Thr Leu
1               5                   10                  15

Ser Gln Ala Ser Pro Val Leu Tyr Thr Arg Glu Asp Thr Thr Ser Asn
            20                  25                  30

Thr Thr Tyr Ala Phe Thr Asn Ser Asn Gly Leu Asn Phe Thr Gln Met
        35                  40                  45

Asn Thr Thr Leu Pro Asn Val Thr Ile Phe Ala Thr Gly Gly Thr Ile
    50                  55                  60

Ala Gly Ser Ala Ala Ser Asn Thr Ala Thr Thr Gly Tyr Gln Ala Gly
65                  70                  75                  80

Ala Leu Gly Ile Gln Thr Leu Ile Asp Ala Val Pro Glu Met Leu Ser
                85                  90                  95

Val Ala Asn Ile Ala Gly Val Gln Ile Ser Asn Val Gly Ser Pro Asp
            100                 105                 110

Val Thr Ser Thr Ile Leu Leu Glu Met Ala His Arg Leu Asn Lys Val
        115                 120                 125

Val Cys Glu Asp Pro Ser Met Ala Gly Ala Val Val Thr His Gly Thr
    130                 135                 140

Asp Thr Leu Glu Glu Thr Ala Phe Phe Leu Asp Ala Thr Val Asn Cys
145                 150                 155                 160

Gly Lys Pro Ile Val Ile Val Gly Ala Met Arg Pro Ala Thr Phe Ile
                165                 170                 175

Ser Ala Asp Gly Pro Tyr Asn Leu Leu Gln Ala Val Thr Val Ala Ser
            180                 185                 190

Thr Lys Glu Ala Arg Asn Arg Gly Ala Met Val Val Met Asn Asp Arg
        195                 200                 205

Ile Ala Ser Ala Tyr Tyr Val Ser Lys Thr Asn Ala Asn Thr Met Asp
    210                 215                 220

Thr Phe Lys Ala Val Glu Met Gly Tyr Leu Gly Ala Ile Ile Ser Asn
225                 230                 235                 240

Thr Pro Phe Phe Tyr Tyr Pro Ala Val Gln Pro Ser Gly Lys Thr Thr
```

-continued

```
                245                 250                 255
Val Asp Val Ser Asn Val Thr Ser Ile Pro Arg Val Asp Ile Leu Tyr
            260                 265                 270

Ser Phe Gln Asp Met Thr Asn Asp Thr Leu Tyr Ser Ser Ile Glu Asn
            275                 280                 285

Gly Ala Lys Gly Val Val Ile Ala Gly Ser Gly Ala Gly Ser Val Asp
            290                 295                 300

Thr Ala Phe Ser Thr Ala Ile Asp Asp Ile Ile Ser Asn Gln Gly Val
305                 310                 315                 320

Pro Ile Val Gln Ser Thr Arg Thr Gly Asn Gly Glu Val Pro Tyr Ser
            325                 330                 335

Ala Glu Gly Gly Ile Ser Ser Gly Phe Leu Asn Pro Ala Lys Ser Arg
            340                 345                 350

Ile Leu Leu Gly Leu Leu Ala Gln Gly Gly Lys Gly Thr Glu Glu
            355                 360                 365

Ile Arg Ala Val Phe Gly Lys Val Ala Val
            370                 375
```

<210> SEQ ID NO 5
<211> LENGTH: 1330
<212> TYPE: DNA
<213> ORGANISM: Aspergillus fumigatus
<220> FEATURE:
<221> NAME/KEY: CDS
<222> LOCATION: (93)..(978)
<220> FEATURE:
<221> NAME/KEY: CDS
<222> LOCATION: (1056)..(1291)

<400> SEQUENCE: 5

```
gccctacgat actttgttga taccgttgcc tggcgtgtac agcgatttca ctccctcgaa      60
agcagagcag ttcgcctcgt cagatcgcaa ag atg acc aaa ctc agc ttc aaa       113
                                   Met Thr Lys Leu Ser Phe Lys
                                    1               5 atc atc aca ctc gcg gct atg ata gcc gtt ggg aat gcc tct ccg ttt      161
Ile Ile Thr Leu Ala Ala Met Ile Ala Val Gly Asn Ala Ser Pro Phe
        10                  15                  20 gtc tac ccc cga gca acc agc cca aac agt aca tat gtc ttc acc aac      209
Val Tyr Pro Arg Ala Thr Ser Pro Asn Ser Thr Tyr Val Phe Thr Asn
    25                  30                  35 tcg cat ggc ttg aac ttc acc cag atg aac acg acg ctc cct aat gtc      257
Ser His Gly Leu Asn Phe Thr Gln Met Asn Thr Thr Leu Pro Asn Val
40                  45                  50                  55 acc atc ctc gca acc ggc ggt acc att gcc ggc tcc agc aac gac aac      305
Thr Ile Leu Ala Thr Gly Gly Thr Ile Ala Gly Ser Ser Asn Asp Asn
            60                  65                  70 acc gcc aca aca ggc tac acg gcc ggc gcg atc ggc atc cag cag ctc      353
Thr Ala Thr Thr Gly Tyr Thr Ala Gly Ala Ile Gly Ile Gln Gln Leu
        75                  80                  85 atg gat gcc gtc cct gag atg cta gac gtt gct aac gtg gcc ggc atc      401
Met Asp Ala Val Pro Glu Met Leu Asp Val Ala Asn Val Ala Gly Ile
        90                  95                 100 cag gtc gcc aat gtc ggc agc ccc gac gtg acg tct tcc ctt ctg ctc      449
Gln Val Ala Asn Val Gly Ser Pro Asp Val Thr Ser Ser Leu Leu Leu
    105                 110                 115 cac atg gcc agg acc atc aac gag gtc gtc tgc gac gac ccc acc atg      497
His Met Ala Arg Thr Ile Asn Glu Val Val Cys Asp Asp Pro Thr Met
120                 125                 130                 135 agc ggc gcc gtc atc acg cac ggc acc gac acg ctc gag gag acg gcc      545
```

```
Ser Gly Ala Val Ile Thr His Gly Thr Asp Thr Leu Glu Glu Thr Ala
                140                 145                 150 ttc ttc ctc gac gct aca gtc aac tgc ggc aag ccc atc gtc gtc gtc        593
Phe Phe Leu Asp Ala Thr Val Asn Cys Gly Lys Pro Ile Val Val Val
            155                 160                 165 ggc gcc atg cgg ccc gca acc gcc atc tcc gcc gac ggc ccg ttc aac        641
Gly Ala Met Arg Pro Ala Thr Ala Ile Ser Ala Asp Gly Pro Phe Asn
        170                 175                 180 ctc ctc cag gcc gtg acc gtc gcc gcg cac ccc act gcg cgc aac cgt        689
Leu Leu Gln Ala Val Thr Val Ala Ala His Pro Thr Ala Arg Asn Arg
    185                 190                 195 ggt gcg ctg gtc gtc atg aac gac cgc att gtg tcc gcg tac tac gtc        737
Gly Ala Leu Val Val Met Asn Asp Arg Ile Val Ser Ala Tyr Tyr Val
200                 205                 210                 215 tcc aag aca aac gcc aac acc atg gac acc ttc aag gcc gtc gag atg        785
Ser Lys Thr Asn Ala Asn Thr Met Asp Thr Phe Lys Ala Val Glu Met
                220                 225                 230 ggc aac ctc ggc gcc atc atc tcc aac aag ccg tac ttc ttt tac ccg        833
Gly Asn Leu Gly Ala Ile Ile Ser Asn Lys Pro Tyr Phe Phe Tyr Pro
            235                 240                 245 ccc gtc atg ccc acc ggt aag acc act ttc gac gtg cgc aac gtc gcc        881
Pro Val Met Pro Thr Gly Lys Thr Thr Phe Asp Val Arg Asn Val Ala
        250                 255                 260 tcc atc ccc aga gtc gac atc ctc tac tcg tac cag gat atg caa aac        929
Ser Ile Pro Arg Val Asp Ile Leu Tyr Ser Tyr Gln Asp Met Gln Asn
    265                 270                 275 gat acg ctc tac gac gcc gtc gac aac ggc gcg aaa ggc atc gtc gta a      978
Asp Thr Leu Tyr Asp Ala Val Asp Asn Gly Ala Lys Gly Ile Val Val
280                 285                 290                 295 gtccagcccc tttctaaagc cctcaccgga tcaaccgctg aaattgaacc taatccagat     1038
cgccggctcc ggcgcag ga  agc gtc tca agt ggc tac tac gat gcc atc        1087
                      Arg Ser Val Ser Ser Gly Tyr Tyr Asp Ala Ile
                                      300                 305 gac gac atc gca tcc acg cac tcc ctc cct gtc gtc ctc agc act cgc        1135
Asp Asp Ile Ala Ser Thr His Ser Leu Pro Val Val Leu Ser Thr Arg
        310                 315                 320 acc ggc aac ggc gaa gtc gcc atc aca gac agc gag acc aca att gag        1183
Thr Gly Asn Gly Glu Val Ala Ile Thr Asp Ser Glu Thr Thr Ile Glu
    325                 330                 335 agc ggc ttc ctg aac ccg cag aaa gcg cgc atc ctc ctc ggt ctg ctg        1231
Ser Gly Phe Leu Asn Pro Gln Lys Ala Arg Ile Leu Leu Gly Leu Leu
340                 345                 350 ctt gct gag gat aag gga ttc aag gag atc aaa gag gcg ttc gcg aag        1279
Leu Ala Glu Asp Lys Gly Phe Lys Glu Ile Lys Glu Ala Phe Ala Lys
355                 360                 365                 370 aac ggg gtt gct tgattatgtc cttccttgtt ttgggtggca tttgtggtt            1330
Asn Gly Val Ala <210> SEQ ID NO 6
<211> LENGTH: 374
<212> TYPE: PRT
<213> ORGANISM: Aspergillus fumigatus

<400> SEQUENCE: 6

Met Thr Lys Leu Ser Phe Lys Ile Ile Thr Leu Ala Ala Met Ile Ala
1               5                   10                  15

Val Gly Asn Ala Ser Pro Phe Val Tyr Pro Arg Ala Thr Ser Pro Asn
            20                  25                  30

Ser Thr Tyr Val Phe Thr Asn Ser His Gly Leu Asn Phe Thr Gln Met
```

```
                 35                  40                  45
Asn Thr Thr Leu Pro Asn Val Thr Ile Leu Ala Thr Gly Gly Thr Ile
 50                  55                  60

Ala Gly Ser Ser Asn Asp Asn Thr Ala Thr Gly Tyr Thr Ala Gly
 65                  70                  75                  80

Ala Ile Gly Ile Gln Gln Leu Met Asp Ala Val Pro Glu Met Leu Asp
                 85                  90                  95

Val Ala Asn Val Ala Gly Ile Gln Val Ala Asn Val Gly Ser Pro Asp
                100                 105                 110

Val Thr Ser Ser Leu Leu Leu His Met Ala Arg Thr Ile Asn Glu Val
                115                 120                 125

Val Cys Asp Asp Pro Thr Met Ser Gly Ala Val Ile Thr His Gly Thr
130                 135                 140

Asp Thr Leu Glu Glu Thr Ala Phe Phe Leu Asp Ala Thr Val Asn Cys
145                 150                 155                 160

Gly Lys Pro Ile Val Val Gly Ala Met Arg Pro Ala Thr Ala Ile
                165                 170                 175

Ser Ala Asp Gly Pro Phe Asn Leu Leu Gln Ala Val Thr Val Ala Ala
                180                 185                 190

His Pro Thr Ala Arg Asn Arg Gly Ala Leu Val Val Met Asn Asp Arg
                195                 200                 205

Ile Val Ser Ala Tyr Tyr Val Ser Lys Thr Asn Ala Asn Thr Met Asp
210                 215                 220

Thr Phe Lys Ala Val Glu Met Gly Asn Leu Gly Ala Ile Ile Ser Asn
225                 230                 235                 240

Lys Pro Tyr Phe Phe Tyr Pro Pro Val Met Pro Thr Gly Lys Thr Thr
                245                 250                 255

Phe Asp Val Arg Asn Val Ala Ser Ile Pro Arg Val Asp Ile Leu Tyr
                260                 265                 270

Ser Tyr Gln Asp Met Gln Asn Asp Thr Leu Tyr Asp Ala Val Asp Asn
                275                 280                 285

Gly Ala Lys Gly Ile Val Val Arg Ser Val Ser Ser Gly Tyr Tyr Asp
290                 295                 300

Ala Ile Asp Asp Ile Ala Ser Thr His Ser Leu Pro Val Val Leu Ser
305                 310                 315                 320

Thr Arg Thr Gly Asn Gly Glu Val Ala Ile Thr Asp Ser Glu Thr Thr
                325                 330                 335

Ile Glu Ser Gly Phe Leu Asn Pro Gln Lys Ala Arg Ile Leu Leu Gly
                340                 345                 350

Leu Leu Leu Ala Glu Asp Lys Gly Phe Lys Glu Ile Lys Glu Ala Phe
                355                 360                 365

Ala Lys Asn Gly Val Ala
                370

<210> SEQ ID NO 7
<211> LENGTH: 1260
<212> TYPE: DNA
<213> ORGANISM: Fusarium graminearum
<220> FEATURE:
<221> NAME/KEY: CDS
<222> LOCATION: (105)..(1217)

<400> SEQUENCE: 7
ctgcgatcgc agaggaggag cagtcttttt cttctcgttc tttacctccc ccctcctcta      60
tctccagtct ctccaagtgt tgtgccctct tgtgttagcc cagc atg tcg ccc tct     116
```

```
                                  Met Ser Pro Ser
                                    1 ttc cac tcc cta ctc gct atc gca acc ctt gca ggc tca gct gcc ctt    164
Phe His Ser Leu Leu Ala Ile Ala Thr Leu Ala Gly Ser Ala Ala Leu
 5           10              15                  20 gca tcc ccg atc ccg gag cca gaa aca ccg cag ctt atc ccc cgg gct    212
Ala Ser Pro Ile Pro Glu Pro Glu Thr Pro Gln Leu Ile Pro Arg Ala
             25              30              35 gtt ggt gac ttt gag tgc ttc aac gct agt ctt ccc aac atc acc atc    260
Val Gly Asp Phe Glu Cys Phe Asn Ala Ser Leu Pro Asn Ile Thr Ile
         40              45              50 ttc gcg act ggt ggt acc atc gct ggt tct gct ggt tct gcc gat cag    308
Phe Ala Thr Gly Gly Thr Ile Ala Gly Ser Ala Gly Ser Ala Asp Gln
             55              60              65 act acg ggt tac cag gct ggt gca ttg ggt atc caa gcg ttg atc gac    356
Thr Thr Gly Tyr Gln Ala Gly Ala Leu Gly Ile Gln Ala Leu Ile Asp
 70              75              80 gct gtc ccg caa ctc tgc aac gtc tcc aac gtc agg ggt gtg cag atc    404
Ala Val Pro Gln Leu Cys Asn Val Ser Asn Val Arg Gly Val Gln Ile
85              90              95             100 gcc aac gtt gat agc ggc gat gta aac tct act atc ctg acc act ttg    452
Ala Asn Val Asp Ser Gly Asp Val Asn Ser Thr Ile Leu Thr Thr Leu
                105             110             115 gcg cat cgc atc cag act gat ctt gac aac cct cac atc caa ggt gtt    500
Ala His Arg Ile Gln Thr Asp Leu Asp Asn Pro His Ile Gln Gly Val
            120             125             130 gtc gtc acc cat ggc aca gac act ctc gag gag tct tca ttt ttc ctc    548
Val Val Thr His Gly Thr Asp Thr Leu Glu Glu Ser Ser Phe Phe Leu
            135             140             145 gat ctc act gtc caa agt gaa aag cct gtt gtt atg gtt gga tcc atg    596
Asp Leu Thr Val Gln Ser Glu Lys Pro Val Val Met Val Gly Ser Met
        150             155             160 cgt cct gcc act gcc atc agc gct gat ggt ccc atc aac ctc ctg tct    644
Arg Pro Ala Thr Ala Ile Ser Ala Asp Gly Pro Ile Asn Leu Leu Ser
165             170             175             180 gct gtt cga ttg gca ggt agc aag agt gcc aag ggt cgc ggt aca atg    692
Ala Val Arg Leu Ala Gly Ser Lys Ser Ala Lys Gly Arg Gly Thr Met
            185             190             195 att gta ctc aac gac aag atc gct tct gca cgc tac acc gtt aaa tcc    740
Ile Val Leu Asn Asp Lys Ile Ala Ser Ala Arg Tyr Thr Val Lys Ser
        200             205             210 cac gcc aat gct gtc cag act ttc att gcc gaa gat caa ggt tat ctt    788
His Ala Asn Ala Val Gln Thr Phe Ile Ala Glu Asp Gln Gly Tyr Leu
        215             220             225 ggt gcc ttt gaa aac att cag ccc gtc ttc tgg tac cct gct agt cga    836
Gly Ala Phe Glu Asn Ile Gln Pro Val Phe Trp Tyr Pro Ala Ser Arg
    230             235             240 cca cta ggt cac cac tat ttc aac att agt gct agc tca cct aag aag    884
Pro Leu Gly His His Tyr Phe Asn Ile Ser Ala Ser Ser Pro Lys Lys
245             250             255             260 gct ctt cct cag gtt gac gtt ttg tac ggc cac caa gaa gcg gac ccc    932
Ala Leu Pro Gln Val Asp Val Leu Tyr Gly His Gln Glu Ala Asp Pro
            265             270             275 gag ctt ttc caa gct gct gtc gat agc ggc gcc cag ggc att gtt ctc    980
Glu Leu Phe Gln Ala Ala Val Asp Ser Gly Ala Gln Gly Ile Val Leu
        280             285             290 gct ggt ctt ggc gct gga ggc tgg cct gac gaa gct gct gat gag atc   1028
Ala Gly Leu Gly Ala Gly Gly Trp Pro Asp Glu Ala Ala Asp Glu Ile
    295             300             305
```

```
aag aag gtc ttg aac gag act aac att cct gtt gtt gtc agc cgt cgt    1076
Lys Lys Val Leu Asn Glu Thr Asn Ile Pro Val Val Val Ser Arg Arg
    310                 315                 320 act gct tgg ggt tac gtt gga gag agg cct ttc ggt atc ggt gct ggg    1124
Thr Ala Trp Gly Tyr Val Gly Glu Arg Pro Phe Gly Ile Gly Ala Gly
325                 330                 335                 340 tac ttg aac cct tcc aag gcc aga atc caa ctg caa ctt gcg ctt gag    1172
Tyr Leu Asn Pro Ser Lys Ala Arg Ile Gln Leu Gln Leu Ala Leu Glu
                345                 350                 355 aag aag ctt tct gtg gag gag atc caa gac ata ttc gag tat gtt        1217
Lys Lys Leu Ser Val Glu Glu Ile Gln Asp Ile Phe Glu Tyr Val
            360                 365                 370 tgattggaag aggattttga aatgaatcaa tgatatatga tta                    1260

<210> SEQ ID NO 8
<211> LENGTH: 371
<212> TYPE: PRT
<213> ORGANISM: Fusarium graminearum

<400> SEQUENCE: 8

Met Ser Pro Ser Phe His Ser Leu Leu Ala Ile Ala Thr Leu Ala Gly
1               5                   10                  15

Ser Ala Ala Leu Ala Ser Pro Ile Pro Glu Pro Glu Thr Pro Gln Leu
            20                  25                  30

Ile Pro Arg Ala Val Gly Asp Phe Glu Cys Phe Asn Ala Ser Leu Pro
        35                  40                  45

Asn Ile Thr Ile Phe Ala Thr Gly Gly Thr Ile Ala Gly Ser Ala Gly
    50                  55                  60

Ser Ala Asp Gln Thr Thr Gly Tyr Gln Ala Gly Ala Leu Gly Ile Gln
65                  70                  75                  80

Ala Leu Ile Asp Ala Val Pro Gln Leu Cys Asn Val Ser Asn Val Arg
                85                  90                  95

Gly Val Gln Ile Ala Asn Val Asp Ser Gly Asp Val Asn Ser Thr Ile
            100                 105                 110

Leu Thr Thr Leu Ala His Arg Ile Gln Thr Asp Leu Asp Asn Pro His
        115                 120                 125

Ile Gln Gly Val Val Val Thr His Gly Thr Asp Thr Leu Glu Glu Ser
    130                 135                 140

Ser Phe Phe Leu Asp Leu Thr Val Gln Ser Glu Lys Pro Val Val Met
145                 150                 155                 160

Val Gly Ser Met Arg Pro Ala Thr Ala Ile Ser Ala Asp Gly Pro Ile
                165                 170                 175

Asn Leu Leu Ser Ala Val Arg Leu Ala Gly Ser Lys Ser Ala Lys Gly
            180                 185                 190

Arg Gly Thr Met Ile Val Leu Asn Asp Lys Ile Ala Ser Ala Arg Tyr
        195                 200                 205

Thr Val Lys Ser His Ala Asn Ala Val Gln Thr Phe Ile Ala Glu Asp
    210                 215                 220

Gln Gly Tyr Leu Gly Ala Phe Glu Asn Ile Gln Pro Val Phe Trp Tyr
225                 230                 235                 240

Pro Ala Ser Arg Pro Leu Gly His His Tyr Phe Asn Ile Ser Ala Ser
                245                 250                 255

Ser Pro Lys Lys Ala Leu Pro Gln Val Asp Val Leu Tyr Gly His Gln
            260                 265                 270

Glu Ala Asp Pro Glu Leu Phe Gln Ala Ala Val Asp Ser Gly Ala Gln
        275                 280                 285
```

```
Gly Ile Val Leu Ala Gly Leu Gly Ala Gly Gly Trp Pro Asp Glu Ala
        290                 295                 300

Ala Asp Glu Ile Lys Lys Val Leu Asn Glu Thr Asn Ile Pro Val Val
305                 310                 315                 320

Val Ser Arg Arg Thr Ala Trp Gly Tyr Val Gly Glu Arg Pro Phe Gly
                325                 330                 335

Ile Gly Ala Gly Tyr Leu Asn Pro Ser Lys Ala Arg Ile Gln Leu Gln
            340                 345                 350

Leu Ala Leu Glu Lys Lys Leu Ser Val Glu Glu Ile Gln Asp Ile Phe
        355                 360                 365

Glu Tyr Val
    370

<210> SEQ ID NO 9
<211> LENGTH: 1470
<212> TYPE: DNA
<213> ORGANISM: Fusarium graminearum
<220> FEATURE:
<221> NAME/KEY: CDS
<222> LOCATION: (77)..(1429)

<400> SEQUENCE: 9
aggacaagcg tccatgaagc ataactacgc tacattgcct ttagctacag ttgatctata      60
gatatcagtc tacatc atg atg ccc agc gtc aga aga ttt cac ggc cag act     112
                  Met Met Pro Ser Val Arg Arg Phe His Gly Gln Thr
                    1               5                  10 atg gtc gcc gcc gct cct tct att tgc tca ggg cct gca gca tcg tcc       160
Met Val Ala Ala Ala Pro Ser Ile Cys Ser Gly Pro Ala Ala Ser Ser
        15                  20                  25 acc atc aag atg gct tca tcg tca gct tcg tgg acg act tat ctg tgg       208
Thr Ile Lys Met Ala Ser Ser Ser Ala Ser Trp Thr Thr Tyr Leu Trp
    30                  35                  40 cgg ctt atc cta gct gtg ctg gct cct tca acg gcc ctg ctg cct ttt       256
Arg Leu Ile Leu Ala Val Leu Ala Pro Ser Thr Ala Leu Leu Pro Phe
45                  50                  55                  60 ggt gcg tgg gtt gtt tcg gtc tgg gga tct cct gtc ctc gac cta cac       304
Gly Ala Trp Val Val Ser Val Trp Gly Ser Pro Val Leu Asp Leu His
                65                  70                  75 gtc caa cct cac ttc tcg gtt caa caa aaa gcg cca ata cag acg ggc       352
Val Gln Pro His Phe Ser Val Gln Gln Lys Ala Pro Ile Gln Thr Gly
            80                  85                  90 atc cct ttc gaa att tcg acc acc tca gga ttc aac tgc ttc aat ccc       400
Ile Pro Phe Glu Ile Ser Thr Thr Ser Gly Phe Asn Cys Phe Asn Pro
        95                 100                 105 aat ctt ccc aac gtc act att tat gcc acc gga ggt act att gct ggc       448
Asn Leu Pro Asn Val Thr Ile Tyr Ala Thr Gly Gly Thr Ile Ala Gly
    110                 115                 120 tcc gca agc tcg gct gat cag acc acg gga tac cgg tca gct gcg tta       496
Ser Ala Ser Ser Ala Asp Gln Thr Thr Gly Tyr Arg Ser Ala Ala Leu
125                 130                 135                 140 gga gtt gat tct ctc att gat gca gta ccc caa ttg tgc aat gta gcc       544
Gly Val Asp Ser Leu Ile Asp Ala Val Pro Gln Leu Cys Asn Val Ala
                145                 150                 155 aat gtg aga ggt gtc cag ttt gcc aac acg gac agc ata gac atg agc       592
Asn Val Arg Gly Val Gln Phe Ala Asn Thr Asp Ser Ile Asp Met Ser
            160                 165                 170 tcg gcc atg ttg agg act ttg gcg aag cag atc cag aat gat ctg gac       640
Ser Ala Met Leu Arg Thr Leu Ala Lys Gln Ile Gln Asn Asp Leu Asp
        175                 180                 185
```

```
agt ccg ttt act caa ggc gca gtt gtg acg cac gga act gat act ctg    688
Ser Pro Phe Thr Gln Gly Ala Val Val Thr His Gly Thr Asp Thr Leu
    190                 195                 200 gat gaa tct gcc ttc ttt ctg gat ctt act atc cag agc gac aag ccc    736
Asp Glu Ser Ala Phe Phe Leu Asp Leu Thr Ile Gln Ser Asp Lys Pro
205                 210                 215                 220 gtg gtc gtg aca ggc tca atg cgc ccg gca act gct atc agc gca gat    784
Val Val Val Thr Gly Ser Met Arg Pro Ala Thr Ala Ile Ser Ala Asp
                225                 230                 235 gga cca atg aat ctt ttg tca tcg gtg aca ttg gca gca gca gcg agt    832
Gly Pro Met Asn Leu Leu Ser Ser Val Thr Leu Ala Ala Ala Ala Ser
            240                 245                 250 gct cga ggc aga gga gtg atg att gcc atg aat gat cgc att gga tct    880
Ala Arg Gly Arg Gly Val Met Ile Ala Met Asn Asp Arg Ile Gly Ser
        255                 260                 265 gct cgt ttt acg acc aaa gtc aac gcc aac cat ttg gac gcc ttc caa    928
Ala Arg Phe Thr Thr Lys Val Asn Ala Asn His Leu Asp Ala Phe Gln
    270                 275                 280 gcc cct gac agt ggc atg ctg gga aca ttc gtc aac gtt cag cca gtg    976
Ala Pro Asp Ser Gly Met Leu Gly Thr Phe Val Asn Val Gln Pro Val
285                 290                 295                 300 ttt ttc tat ccg cca tca cga cct ctt ggc cac cgt cat ttt gat ctg   1024
Phe Phe Tyr Pro Pro Ser Arg Pro Leu Gly His Arg His Phe Asp Leu
                305                 310                 315 cgg ccc atc acc aac aac ggc cgc cgg ttc gga cgc tct aca gcc ccc   1072
Arg Pro Ile Thr Asn Asn Gly Arg Arg Phe Gly Arg Ser Thr Ala Pro
            320                 325                 330 gga gca gga tca tca gca cta ccc cag gtg gac gtg ctc tac gct tac   1120
Gly Ala Gly Ser Ser Ala Leu Pro Gln Val Asp Val Leu Tyr Ala Tyr
        335                 340                 345 cag gag ctc agc gtg ggc atg ttc cag gcg gcc atc gac ctt gga gcg   1168
Gln Glu Leu Ser Val Gly Met Phe Gln Ala Ala Ile Asp Leu Gly Ala
    350                 355                 360 cag ggc atc gtt cta gcg gga atg ggc gct gga ttc tgg acg tcc aaa   1216
Gln Gly Ile Val Leu Ala Gly Met Gly Ala Gly Phe Trp Thr Ser Lys
365                 370                 375                 380 ggt acc gag gag att cgg cgt atc gtc cac gag acc gat att ccc gtg   1264
Gly Thr Glu Glu Ile Arg Arg Ile Val His Glu Thr Asp Ile Pro Val
                385                 390                 395 ata gtg agc cga aga ccg gaa ggc ggc ttc gtc gga cca tgt gag gca   1312
Ile Val Ser Arg Arg Pro Glu Gly Gly Phe Val Gly Pro Cys Glu Ala
            400                 405                 410 gga atc ggc gcg ggc ttt ttg aat ccg caa aag gcg agg atc cag ctc   1360
Gly Ile Gly Ala Gly Phe Leu Asn Pro Gln Lys Ala Arg Ile Gln Leu
        415                 420                 425 caa ctg gcc ctg gag acc aag atg gac aat gat gcc atc aaa gcc ctg   1408
Gln Leu Ala Leu Glu Thr Lys Met Asp Asn Asp Ala Ile Lys Ala Leu
    430                 435                 440 ttt gag cat tcg gga gtg cac taaagggaca aaaaagatcg aggttacagc      1459
Phe Glu His Ser Gly Val His
445                 450 agcaacacca c                                                       1470

<210> SEQ ID NO 10
<211> LENGTH: 451
<212> TYPE: PRT
<213> ORGANISM: Fusarium graminearum

<400> SEQUENCE:

-continued

```
Met Met Pro Ser Val Arg Arg Phe His Gly Gln Thr Met Val Ala Ala
1               5                   10                  15

Ala Pro Ser Ile Cys Ser Gly Pro Ala Ser Ser Thr Ile Lys Met
            20                  25                  30

Ala Ser Ser Ala Ser Trp Thr Thr Tyr Leu Trp Arg Leu Ile Leu
                35                  40                  45

Ala Val Leu Ala Pro Ser Thr Ala Leu Leu Pro Phe Gly Ala Trp Val
        50                  55                  60

Val Ser Val Trp Gly Ser Pro Val Leu Asp Leu His Val Gln Pro His
65                  70                  75                  80

Phe Ser Val Gln Gln Lys Ala Pro Ile Gln Thr Gly Ile Pro Phe Glu
                85                  90                  95

Ile Ser Thr Thr Ser Gly Phe Asn Cys Phe Asn Pro Asn Leu Pro Asn
                100                 105                 110

Val Thr Ile Tyr Ala Thr Gly Gly Thr Ile Ala Gly Ser Ala Ser Ser
        115                 120                 125

Ala Asp Gln Thr Thr Gly Tyr Arg Ser Ala Ala Leu Gly Val Asp Ser
    130                 135                 140

Leu Ile Asp Ala Val Pro Gln Leu Cys Asn Val Ala Asn Val Arg Gly
145                 150                 155                 160

Val Gln Phe Ala Asn Thr Asp Ser Ile Asp Met Ser Ser Ala Met Leu
                165                 170                 175

Arg Thr Leu Ala Lys Gln Ile Gln Asn Asp Leu Asp Ser Pro Phe Thr
            180                 185                 190

Gln Gly Ala Val Val Thr His Gly Thr Asp Thr Leu Asp Glu Ser Ala
        195                 200                 205

Phe Phe Leu Asp Leu Thr Ile Gln Ser Asp Lys Pro Val Val Thr
210                 215                 220

Gly Ser Met Arg Pro Ala Thr Ala Ile Ser Ala Asp Gly Pro Met Asn
225                 230                 235                 240

Leu Leu Ser Ser Val Thr Leu Ala Ala Ala Ser Ala Arg Gly Arg
            245                 250                 255

Gly Val Met Ile Ala Met Asn Asp Arg Ile Gly Ser Ala Arg Phe Thr
            260                 265                 270

Thr Lys Val Asn Ala Asn His Leu Asp Ala Phe Gln Ala Pro Asp Ser
        275                 280                 285

Gly Met Leu Gly Thr Phe Val Asn Val Gln Pro Val Phe Tyr Pro
    290                 295                 300

Pro Ser Arg Pro Leu Gly His Arg His Phe Asp Leu Arg Pro Ile Thr
305                 310                 315                 320

Asn Asn Gly Arg Arg Phe Gly Arg Ser Thr Ala Pro Gly Ala Gly Ser
                325                 330                 335

Ser Ala Leu Pro Gln Val Asp Val Leu Tyr Ala Tyr Gln Glu Leu Ser
            340                 345                 350

Val Gly Met Phe Gln Ala Ala Ile Asp Leu Gly Ala Gln Gly Ile Val
        355                 360                 365

Leu Ala Gly Met Gly Ala Gly Phe Trp Thr Ser Lys Gly Thr Glu Glu
        370                 375                 380

Ile Arg Arg Ile Val His Glu Thr Asp Ile Pro Val Ile Val Ser Arg
385                 390                 395                 400

Arg Pro Glu Gly Gly Phe Val Gly Pro Cys Glu Ala Gly Ile Gly Ala
                405                 410                 415

Gly Phe Leu Asn Pro Gln Lys Ala Arg Ile Gln Leu Gln Leu Ala Leu
```

-continued

```
                    420                 425                 430
Glu Thr Lys Met Asp Asn Asp Ala Ile Lys Ala Leu Phe Glu His Ser
            435                 440                 445
Gly Val His
    450

<210> SEQ ID NO 11
<211> LENGTH: 1236
<212> TYPE: DNA
<213> ORGANISM: Penicillium citrinum
<220> FEATURE:
<221> NAME/KEY: CDS
<222> LOCATION: (16)..(1152)

<400> SEQUENCE: 11
acatattgaa acaat atg aga ctt cta ttt aat act ctg gct gtc tca gca        51
                Met Arg Leu Leu Phe Asn Thr Leu Ala Val Ser Ala
                  1               5                  10 cta gct gct acg agt tat gcc tct ccc atc att cat tcc cgg gcc tcc        99
Leu Ala Ala Thr Ser Tyr Ala Ser Pro Ile Ile His Ser Arg Ala Ser
            15                  20                  25 aac acg tcc tat acc aac tct aat ggg ctg aaa ttt aac cat ttc gac       147
Asn Thr Ser Tyr Thr Asn Ser Asn Gly Leu Lys Phe Asn His Phe Asp
        30                  35                  40 gct tct ctt cca aat gtg act ttg ctg gca act ggt gga act att gcc       195
Ala Ser Leu Pro Asn Val Thr Leu Leu Ala Thr Gly Gly Thr Ile Ala
45                  50                  55                  60 ggt aca agc gat gac aag act gct acg gca gga tat gaa tcc ggg gct       243
Gly Thr Ser Asp Asp Lys Thr Ala Thr Ala Gly Tyr Glu Ser Gly Ala
                65                  70                  75 tta ggg ata aat aag att ctt tcc ggc atc cca gaa gtt tat gac att       291
Leu Gly Ile Asn Lys Ile Leu Ser Gly Ile Pro Glu Val Tyr Asp Ile
            80                  85                  90 gcc aac gtc aat gcg gta cag ttt gac aat gtc aac agc ggc gat gtc       339
Ala Asn Val Asn Ala Val Gln Phe Asp Asn Val Asn Ser Gly Asp Val
        95                 100                 105 tct yca tct ctc tta ctg aac atg aca cat acc ctt caa aag acc gtt       387
Ser Xaa Ser Leu Leu Leu Asn Met Thr His Thr Leu Gln Lys Thr Val
    110                 115                 120 tgt gat gac cct acg ata tct ggc gcc gtc atc acc cat ggc acc gat       435
Cys Asp Asp Pro Thr Ile Ser Gly Ala Val Ile Thr His Gly Thr Asp
125                 130                 135                 140 acc ctg gaa gaa tct gcc ttc ttc atc gat gca aca gtc aac tgc ggc       483
Thr Leu Glu Glu Ser Ala Phe Phe Ile Asp Ala Thr Val Asn Cys Gly
                145                 150                 155 aag ccg att gtg ttc gtt ggc tca atg cga cct tcc acc gca atc tct       531
Lys Pro Ile Val Phe Val Gly Ser Met Arg Pro Ser Thr Ala Ile Ser
            160                 165                 170 gcc gat ggc cct atg aat ttg ctc cag gga gtg act gtg gcc gct gac       579
Ala Asp Gly Pro Met Asn Leu Leu Gln Gly Val Thr Val Ala Ala Asp
        175                 180                 185 aaa cag gct aag aac cgc gga gca cta gtc gtg ctg aat gac cgc att       627
Lys Gln Ala Lys Asn Arg Gly Ala Leu Val Val Leu Asn Asp Arg Ile
    190                 195                 200 gtc tct gct ttc ttc gct aca aag aca aat gcg aat aca atg gac act       675
Val Ser Ala Phe Phe Ala Thr Lys Thr Asn Ala Asn Thr Met Asp Thr
205                 210                 215                 220 ttc aag gct tat gaa caa ggc agt ctt ggc atg att gtt tca aac aag       723
Phe Lys Ala Tyr Glu Gln Gly Ser Leu Gly Met Ile Val Ser Asn Lys
                225                 230                 235
```

```
ccc tac ttc tat tat ccg gca gtc gag cca aac gcg aag cac gtt gtt        771
Pro Tyr Phe Tyr Tyr Pro Ala Val Glu Pro Asn Ala Lys His Val Val
            240                 245                 250 cat ctt gac gac gtg gat gcg atc ccc cgt gtg gat att ctc tac gct        819
His Leu Asp Asp Val Asp Ala Ile Pro Arg Val Asp Ile Leu Tyr Ala
            255                 260                 265 tac gag gac atg cat agc gac tcc ctt cac agt gct atc aaa aat gga        867
Tyr Glu Asp Met His Ser Asp Ser Leu His Ser Ala Ile Lys Asn Gly
    270                 275                 280 gcc aag ggc atc gtg gtc gcc ggc gag ggc gca ggt ggt atc tcc acg        915
Ala Lys Gly Ile Val Val Ala Gly Glu Gly Ala Gly Gly Ile Ser Thr
285                 290                 295                 300 gac ttt agt gat acc atc gat gag att gca tcg aag cat cag att ccc        963
Asp Phe Ser Asp Thr Ile Asp Glu Ile Ala Ser Lys His Gln Ile Pro
                305                 310                 315 att atc ctg agc cac aga acc gtg aac gga gaa gtt cct act gct gat       1011
Ile Ile Leu Ser His Arg Thr Val Asn Gly Glu Val Pro Thr Ala Asp
            320                 325                 330 att acg ggt gat agc gcg aag act cgc att gca agt ggc atg tat aac       1059
Ile Thr Gly Asp Ser Ala Lys Thr Arg Ile Ala Ser Gly Met Tyr Asn
            335                 340                 345 ccc cag cag gcg cgc gtc ttg ctt gga cta ttg ctc gca gaa ggc aag       1107
Pro Gln Gln Ala Arg Val Leu Leu Gly Leu Leu Leu Ala Glu Gly Lys
    350                 355                 360 aag ttt gag gat att cga act atc ttc gga aaa gct act gtt gcc            1152
Lys Phe Glu Asp Ile Arg Thr Ile Phe Gly Lys Ala Thr Val Ala
365                 370                 375 tagacccacg tcatatatta tgcccatact tgggaacact tgaaactgat agactaaatt     1212
aattatattg tcgtttgttg ccgg                                            1236

<210> SEQ ID NO 12
<211> LENGTH: 379
<212> TYPE: PRT
<213> ORGANISM: Penicillium citrinum
<220> FEATURE:
<221> NAME/KEY: misc_feature
<222> LOCATION: (110)..(110)
<223> OTHER INFORMATION: The 'Xaa' at location 110 stands for Pro, or
      Ser.

<400> SEQUENCE: 12

Met Arg Leu Leu Phe Asn Thr Leu Ala Val Ser Ala Leu Ala Ala Thr
1               5                   10                  15

Ser Tyr Ala Ser Pro Ile Ile His Ser Arg Ala Ser Asn Thr Ser Tyr
            20                  25                  30

Thr Asn Ser Asn Gly Leu Lys Phe Asn His Phe Asp Ala Ser Leu Pro
        35                  40                  45

Asn Val Thr Leu Leu Ala Thr Gly Gly Thr Ile Ala Gly Thr Ser Asp
    50                  55                  60

Asp Lys Thr Ala Thr Ala Gly Tyr Glu Ser Gly Ala Leu Gly Ile Asn
65                  70                  75                  80

Lys Ile Leu Ser Gly Ile Pro Glu Val Tyr Asp Ile Ala Asn Val Asn
                85                  90                  95

Ala Val Gln Phe Asp Asn Val Asn Ser Gly Asp Val Ser Xaa Ser Leu
            100                 105                 110

Leu Leu Asn Met Thr His Thr Leu Gln Lys Thr Val Cys Asp Asp Pro
        115                 120                 125

Thr Ile Ser Gly Ala Val Ile Thr His Gly Thr Asp Thr Leu Glu Glu
    130                 135                 140
```

```
Ser Ala Phe Phe Ile Asp Ala Thr Val Asn Cys Gly Lys Pro Ile Val
145                 150                 155                 160

Phe Val Gly Ser Met Arg Pro Ser Thr Ala Ile Ser Ala Asp Gly Pro
            165                 170                 175

Met Asn Leu Leu Gln Gly Val Thr Val Ala Ala Asp Lys Gln Ala Lys
        180                 185                 190

Asn Arg Gly Ala Leu Val Val Leu Asn Asp Arg Ile Val Ser Ala Phe
    195                 200                 205

Phe Ala Thr Lys Thr Asn Ala Asn Thr Met Asp Thr Phe Lys Ala Tyr
210                 215                 220

Glu Gln Gly Ser Leu Gly Met Ile Val Ser Asn Lys Pro Tyr Phe Tyr
225                 230                 235                 240

Tyr Pro Ala Val Glu Pro Asn Ala Lys His Val His Leu Asp Asp
            245                 250                 255

Val Asp Ala Ile Pro Arg Val Asp Ile Leu Tyr Ala Tyr Glu Asp Met
            260                 265                 270

His Ser Asp Ser Leu His Ser Ala Ile Lys Asn Gly Ala Lys Gly Ile
        275                 280                 285

Val Val Ala Gly Glu Gly Ala Gly Gly Ile Ser Thr Asp Phe Ser Asp
        290                 295                 300

Thr Ile Asp Glu Ile Ala Ser Lys His Gln Ile Pro Ile Ile Leu Ser
305                 310                 315                 320

His Arg Thr Val Asn Gly Glu Val Pro Thr Ala Asp Ile Thr Gly Asp
                325                 330                 335

Ser Ala Lys Thr Arg Ile Ala Ser Gly Met Tyr Asn Pro Gln Gln Ala
            340                 345                 350

Arg Val Leu Leu Gly Leu Leu Ala Glu Gly Lys Lys Phe Glu Asp
        355                 360                 365

Ile Arg Thr Ile Phe Gly Lys Ala Thr Val Ala
    370                 375

<210> SEQ ID NO 13
<211> LENGTH: 362
<212> TYPE: PRT
<213> ORGANISM: Saccharomyces cerevisiae

<400> SEQUENCE: 13

Met Arg Ser Leu Asn Thr Leu Leu Ser Leu Phe Val Ala Met Ser
1               5                   10                  15

Ser Gly Ala Pro Leu Leu Lys Ile Arg Glu Glu Lys Asn Ser Ser Leu
            20                  25                  30

Pro Ser Ile Lys Ile Phe Gly Thr Gly Thr Ile Ala Ser Lys Gly
        35                  40                  45

Ser Thr Ser Ala Thr Thr Ala Gly Tyr Ser Val Gly Leu Thr Val Asn
    50                  55                  60

Asp Leu Ile Glu Ala Val Pro Ser Leu Ala Glu Lys Ala Asn Leu Asp
65                  70                  75                  80

Tyr Leu Gln Val Ser Asn Val Gly Ser Asn Ser Leu Asn Tyr Thr His
                85                  90                  95

Leu Ile Pro Leu Tyr His Gly Ile Ser Glu Ala Leu Ala Ser Asp Asp
            100                 105                 110

Tyr Ala Gly Ala Val Val Thr His Gly Thr Asp Thr Met Glu Glu Thr
        115                 120                 125

Ala Phe Phe Leu Asp Leu Thr Ile Asn Ser Glu Lys Pro Val Cys Ile
```

130                 135                 140
Ala Gly Ala Met Arg Pro Ala Thr Ala Thr Ser Ala Asp Gly Pro Met
145                 150                 155                 160

Asn Leu Tyr Gln Ala Val Ser Ile Ala Ala Ser Glu Lys Ser Leu Gly
                165                 170                 175

Arg Gly Thr Met Ile Thr Leu Asn Asp Arg Ile Ala Ser Gly Phe Trp
            180                 185                 190

Thr Thr Lys Met Asn Ala Asn Ser Leu Asp Thr Phe Arg Ala Asp Glu
            195                 200                 205

Gln Gly Tyr Leu Gly Tyr Phe Ser Asn Asp Asp Val Glu Phe Tyr Tyr
        210                 215                 220

Pro Pro Val Lys Pro Asn Gly Trp Gln Phe Phe Asp Ile Ser Asn Leu
225                 230                 235                 240

Thr Asp Pro Ser Glu Ile Pro Glu Val Ile Ile Leu Tyr Ser Tyr Gln
                245                 250                 255

Gly Leu Asn Pro Glu Leu Ile Val Lys Ala Val Lys Asp Leu Gly Ala
            260                 265                 270

Lys Gly Ile Val Leu Ala Gly Ser Gly Ala Gly Ser Trp Thr Ala Thr
        275                 280                 285

Gly Ser Ile Val Asn Glu Gln Leu Tyr Glu Glu Tyr Gly Ile Pro Ile
        290                 295                 300

Val His Ser Arg Arg Thr Ala Asp Gly Thr Val Pro Pro Asp Asp Ala
305                 310                 315                 320

Pro Glu Tyr Ala Ile Gly Ser Gly Tyr Leu Asn Pro Gln Lys Ser Arg
                325                 330                 335

Ile Leu Leu Gln Leu Cys Leu Tyr Ser Gly Tyr Gly Met Asp Gln Ile
            340                 345                 350

Arg Ser Val Phe Ser Gly Val Tyr Gly Gly
            355                 360

<210> SEQ ID NO 14
<211> LENGTH: 30
<212> TYPE: DNA
<213> ORGANISM: Artificial
<220> FEATURE:
<223> OTHER INFORMATION: Primer AoASP7

<400> SEQUENCE: 14
caaggatcca gcagtatggg tgtcaatttc                               30

<210> SEQ ID NO 15
<211> LENGTH: 28
<212> TYPE: DNA
<213> ORGANISM: Artificial
<220> FEATURE:
<223> OTHER INFORMATION: Primer AoASP8

<400> SEQUENCE: 15
atcaagcttc tattatccat cccatcca                                 28

The invention claimed is:

1. An isolated polypeptide having asparaginase activity and having an amino acid sequence which is at least 95% identical with the amino acid sequence of SEQ ID NO: 2, residues 27-378 of SEQ ID NO:2, residues 30-378 of SEQ ID NO:2, residues 75-378 of SEQ ID NO:2 or residues 80-378 of SEQ ID NO:2.

2. The polypeptide of claim 1, wherein the polypeptide comprises SEQ ID NO: 2.

3. The polypeptide of claim 1, wherein the polypeptide comprises residues 27-378 of SEQ ID NO: 2.

4. The polypeptide of claim 1, wherein the polypeptide comprises residues 30-378 of SEQ ID NO: 2.

5. The polypeptide of claim 1, wherein the polypeptide comprises residues 75-378 of SEQ ID NO: 2.

6. The polypeptide of claim 1, wherein the polypeptide comprises residues 80-378 of SEQ ID NO: 2.

7. The polypeptide of claim 1, wherein the polypeptide is at least 95% identical with SEQ ID NO: 2.

8. The polypeptide of claim 1, wherein the polypeptide is at least 95% identical with residues 27-378 of SEQ ID NO: 2.

9. The polypeptide of claim 1, wherein the polypeptide is at least 95% identical with residues 30-378 of SEQ ID NO: 2.

10. The polypeptide of claim 1, wherein the polypeptide is at least 95% identical with residues 75-378 of SEQ ID NO: 2.

11. The polypeptide of claim 1, wherein the polypeptide is at least 95% identical with residues 80-378 of SEQ ID NO: 2.

12. The polypeptide of claim 1, wherein the polypeptide is at least 98% identical with SEQ ID NO: 2.

13. The polypeptide of claim 1, wherein the polypeptide is at least 98% identical with residues 27-378 of SEQ ID NO: 2.

14. The polypeptide of claim 1, wherein the polypeptide is at least 98% identical with residues 30-378 of SEQ ID NO: 2.

15. The polypeptide of claim 1, wherein the polypeptide is at least 98% identical with residues 75-378 of SEQ ID NO: 2.

16. The polypeptide of claim 1, wherein the polypeptide is at least 98% identical with residues 80-378 of SEQ ID NO: 2.

17. The polypeptide of claim 1, wherein the polypeptide consists of SEQ ID NO: 2.

18. The polypeptide of claim 1, wherein the polypeptide consists of residues 27-378 of SEQ ID NO: 2.

19. The polypeptide of claim 1, wherein the polypeptide consists of residues 30-378 of SEQ ID NO: 2.

20. The polypeptide of claim 1, wherein the polypeptide consists of residues 75-378 of SEQ ID NO: 2.

21. The polypeptide of claim 1, wherein the polypeptide consists of residues 80-378 of SEQ ID NO: 2.

22. A method of preparing a heat-treated product, comprising the sequential steps of:
    a) providing a raw material which comprises carbohydrate, protein and water
    b) treating the raw material with a polypeptide according to claim 1, and
    c) heat treating to reach a final water content below 35% by weight.

23. The method of claim 22 which further comprises treating the raw material with an oxidoreductase capable of reacting with a reducing sugar as a substrate.

24. The method of claim 23 wherein the oxidoreductase capable of reacting with a reducing sugar as a substrate is a glucose oxidase; a pyranose oxidase; a hexose oxidase; a galactose oxidase; or a carbohydrate oxidase which has a higher activity on maltose than on glucose.

25. The method of claim 22 wherein the raw material is in the form of a dough and the enzyme treatment comprises mixing the enzyme into the dough.

26. The method of claim 22 wherein the raw material comprises intact vegetable pieces and the enzyme treatment comprises immersing the vegetable pieces in an aqueous solution of the enzyme.

27. The method of claim 22 wherein the raw material comprises a potato product.

* * * * *